United States Patent [19]

Green

[11] 4,349,028
[45] Sep. 14, 1982

[54] SURGICAL STAPLING APPARATUS HAVING SELF-CONTAINED PNEUMATIC SYSTEM FOR COMPLETING MANUALLY INITIATED MOTION SEQUENCE

[75] Inventor: David T. Green, Norwalk, Conn.

[73] Assignee: United States Surgical Corporation, Norwalk, Conn.

[21] Appl. No.: 190,146

[22] Filed: Oct. 3, 1980

[51] Int. Cl.³ .................. A61B 17/12; A61B 17/32
[52] U.S. Cl. ................... 128/305; 128/325; 128/334 R; 227/19; 227/DIG. 1
[58] Field of Search ............ 128/334 R, 303 R, 326, 128/305, 325; 227/DIG. 1, 19; 29/243.56

[56] References Cited

U.S. PATENT DOCUMENTS

| | | | |
|---|---|---|---|
| 1,451,717 | 4/1923 | Sommer. | |
| 2,487,475 | 11/1949 | Powers | 1/49 |
| 3,006,344 | 10/1961 | Vogelfanger | 128/318 |
| 3,079,608 | 3/1963 | Babkin | 1/187 |
| 3,160,890 | 12/1964 | Lefebvre | 1/187 |
| 3,287,955 | 11/1966 | Winslow et al. | 72/407 |
| 3,613,507 | 10/1971 | Smith, Jr. | 91/398 |
| 3,618,842 | 11/1971 | Bryan | 227/138 |
| 3,643,851 | 2/1972 | Green et al. | 227/19 |
| 3,653,117 | 4/1972 | Wolfberg et al. | 29/429 |
| 3,662,939 | 5/1972 | Bryan | 227/19 |
| 3,665,924 | 5/1972 | Noiles et al. | 128/305 |
| 3,675,688 | 7/1972 | Bryan et al. | 140/93 D |
| 3,683,927 | 8/1972 | Noiles | 128/334 R |
| 3,717,294 | 2/1973 | Green | 227/19 |
| 3,735,762 | 5/1973 | Bryan et al. | 128/305 |
| 3,740,994 | 6/1973 | De Carlo, Jr. | 72/407 |
| 3,815,476 | 6/1974 | Green et al. | 91/410 |
| 3,837,555 | 9/1974 | Green | 227/130 |
| 3,889,683 | 6/1975 | Kapitanov et al. | 128/305 |
| 3,955,581 | 5/1976 | Spasiano et al. | 128/334 R |
| 4,086,926 | 5/1978 | Green et al. | 128/334 R |

Primary Examiner—Michael H. Thaler
Attorney, Agent, or Firm—Robert R. Jackson; John E. Nathan

[57] ABSTRACT

Surgical stapling apparatus has a sequence of motion which is initiated manually and which is thereafter continued automatically by a pneumatic system contained within the apparatus. The pneumatic system uses relatively low pressure gas, and the apparatus has a mechanical linkage between the pneumatic system and the parts driven by the pneumatic system for matching the force available from the pneumatic system to the force required to drive the apparatus during the various portions of the motion sequence. An illustrative embodiment of the invention is ligating and dividing apparatus in which the motion sequence includes clamping tissue in the apparatus, advancing staple-like metal ligatures toward the clamped tissue, crimping the ligatures around the tissue to ligate the tissue, and cutting through the ligated tissue between the ligatures.

17 Claims, 24 Drawing Figures

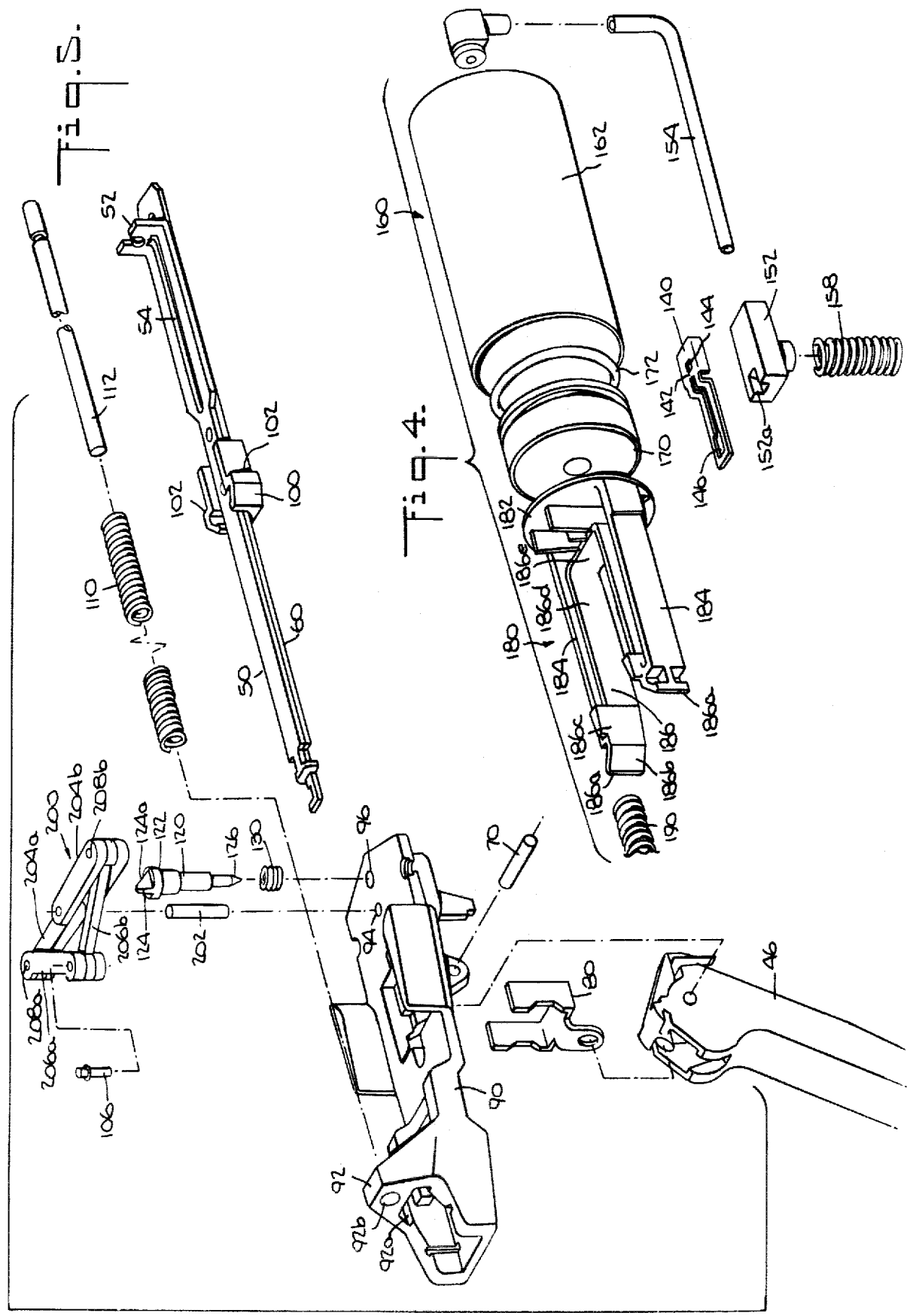

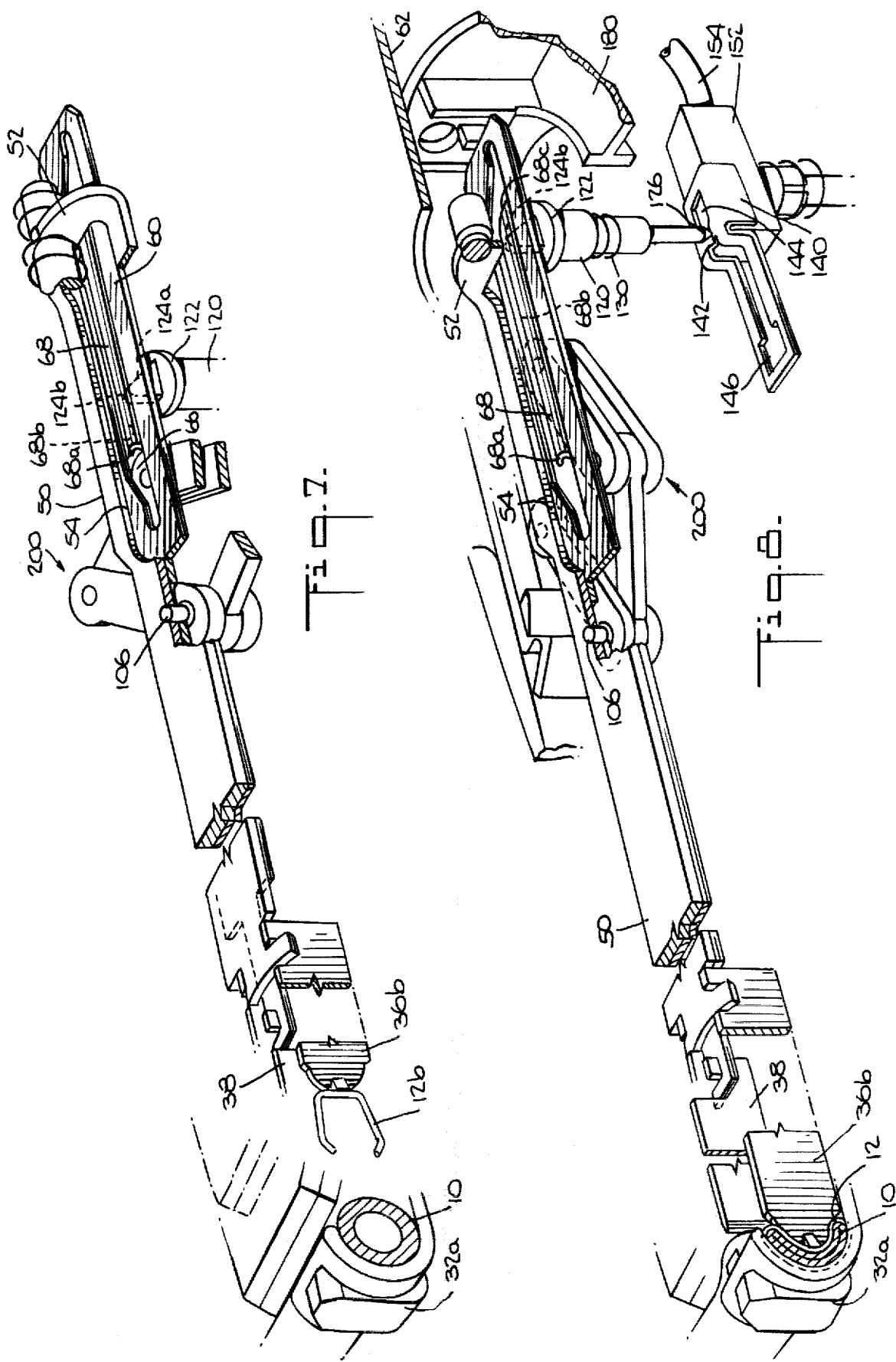

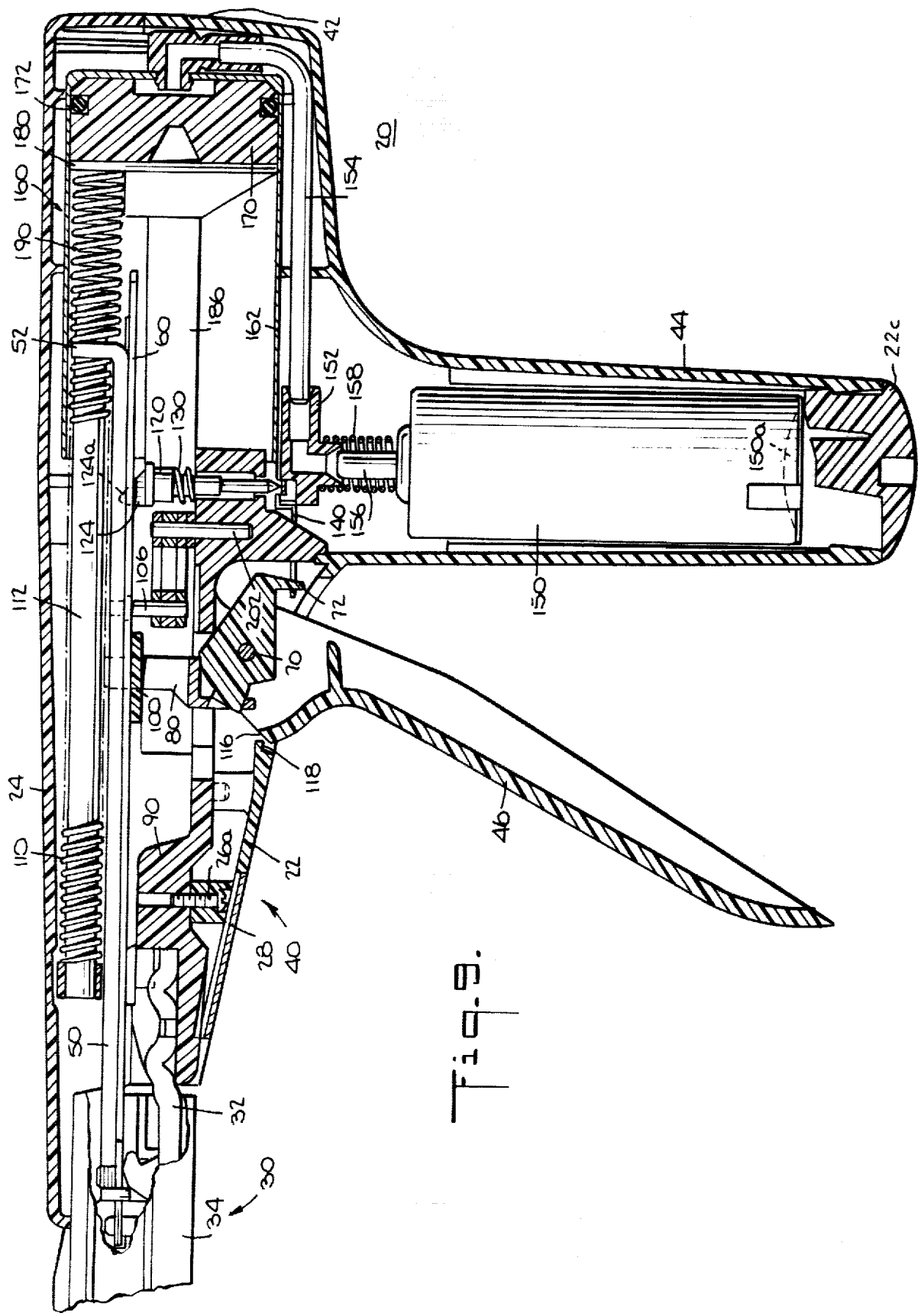

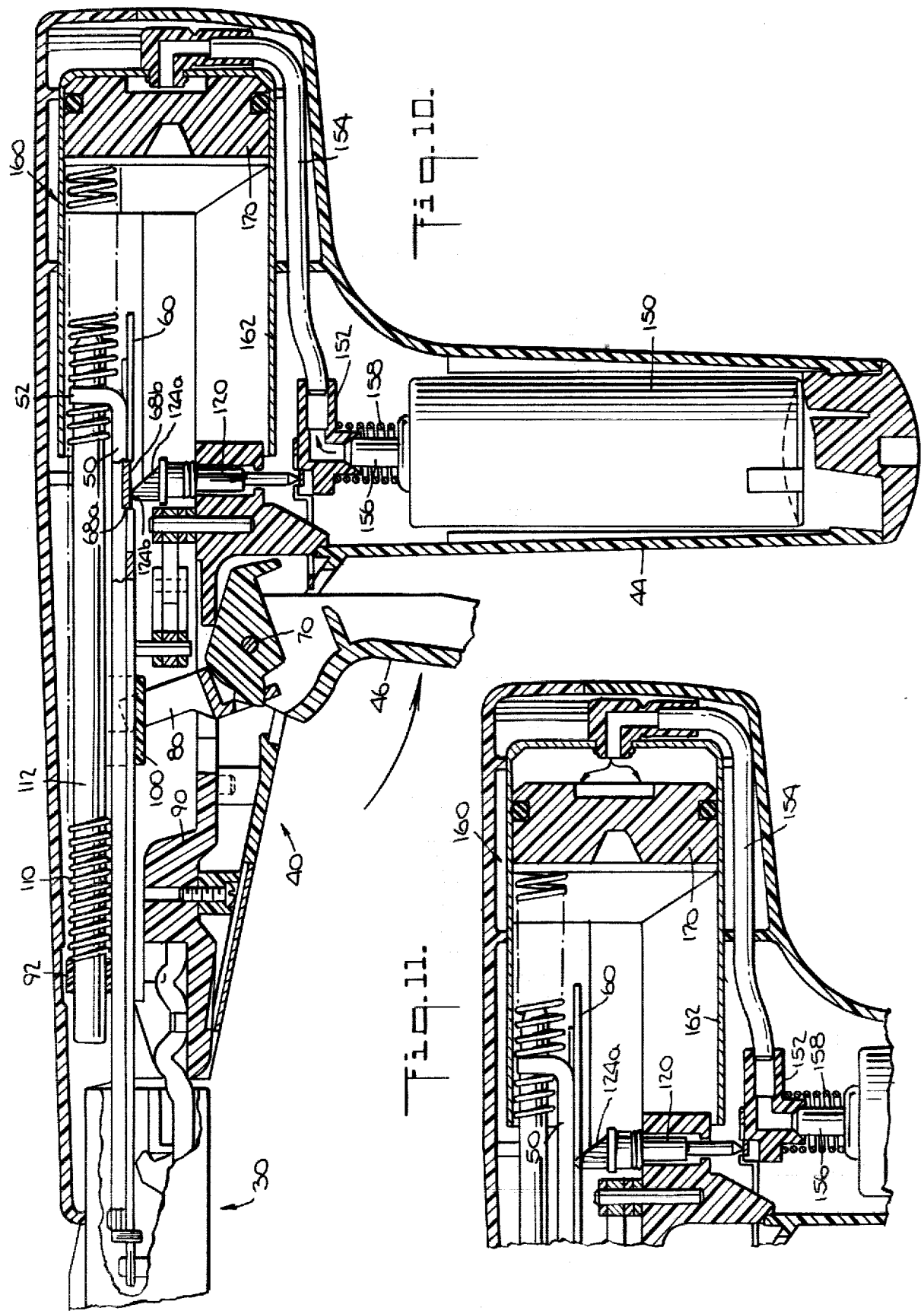

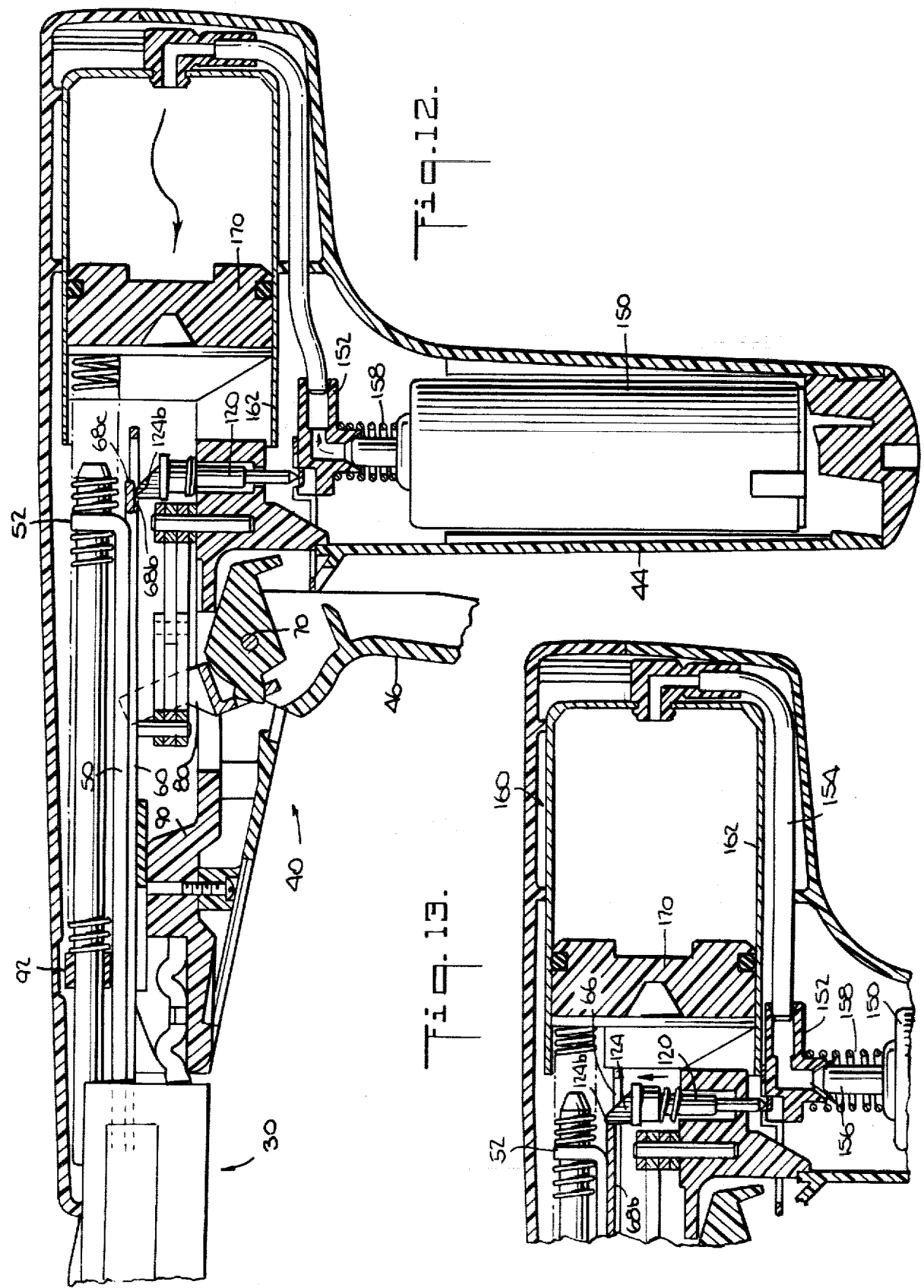

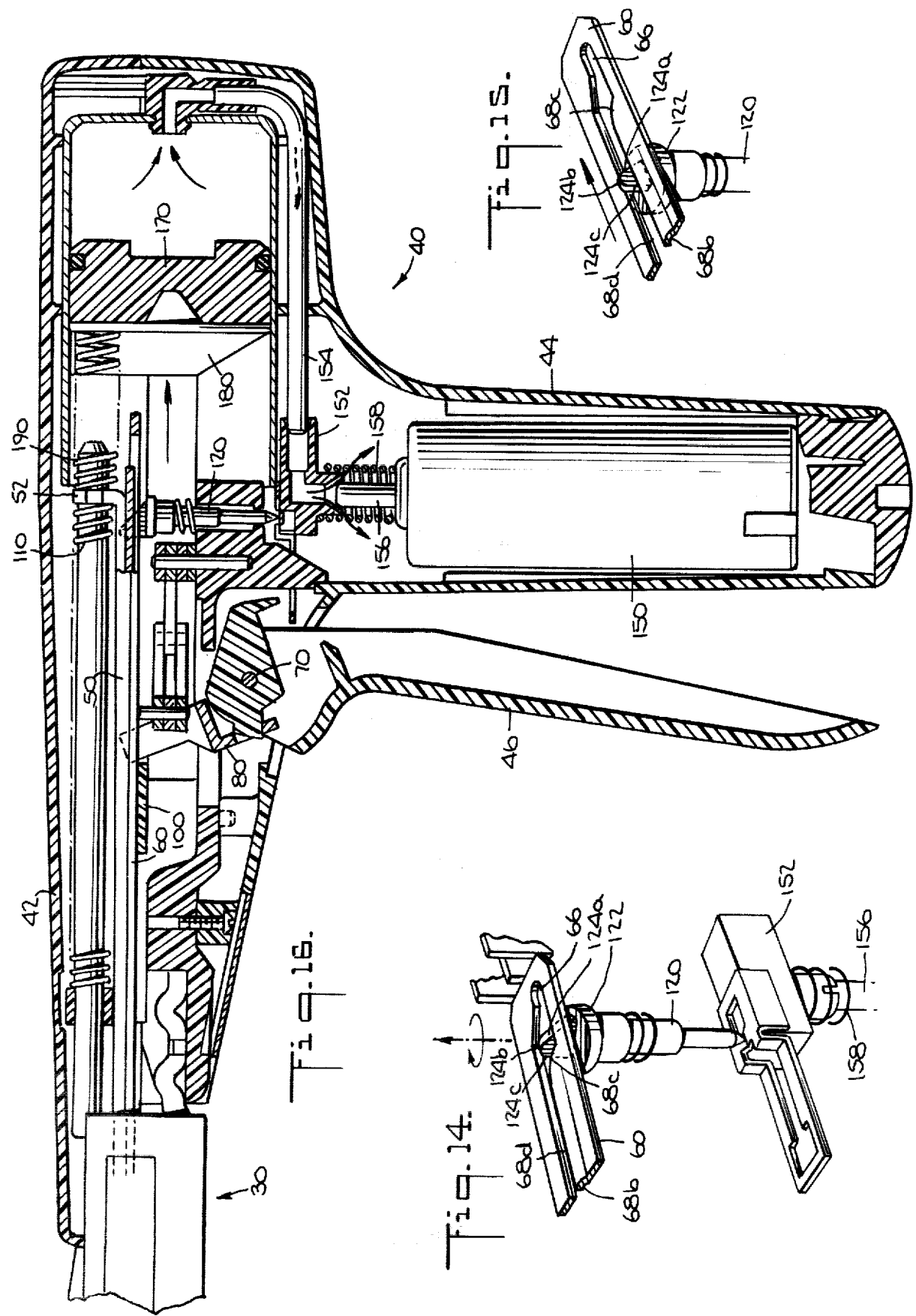

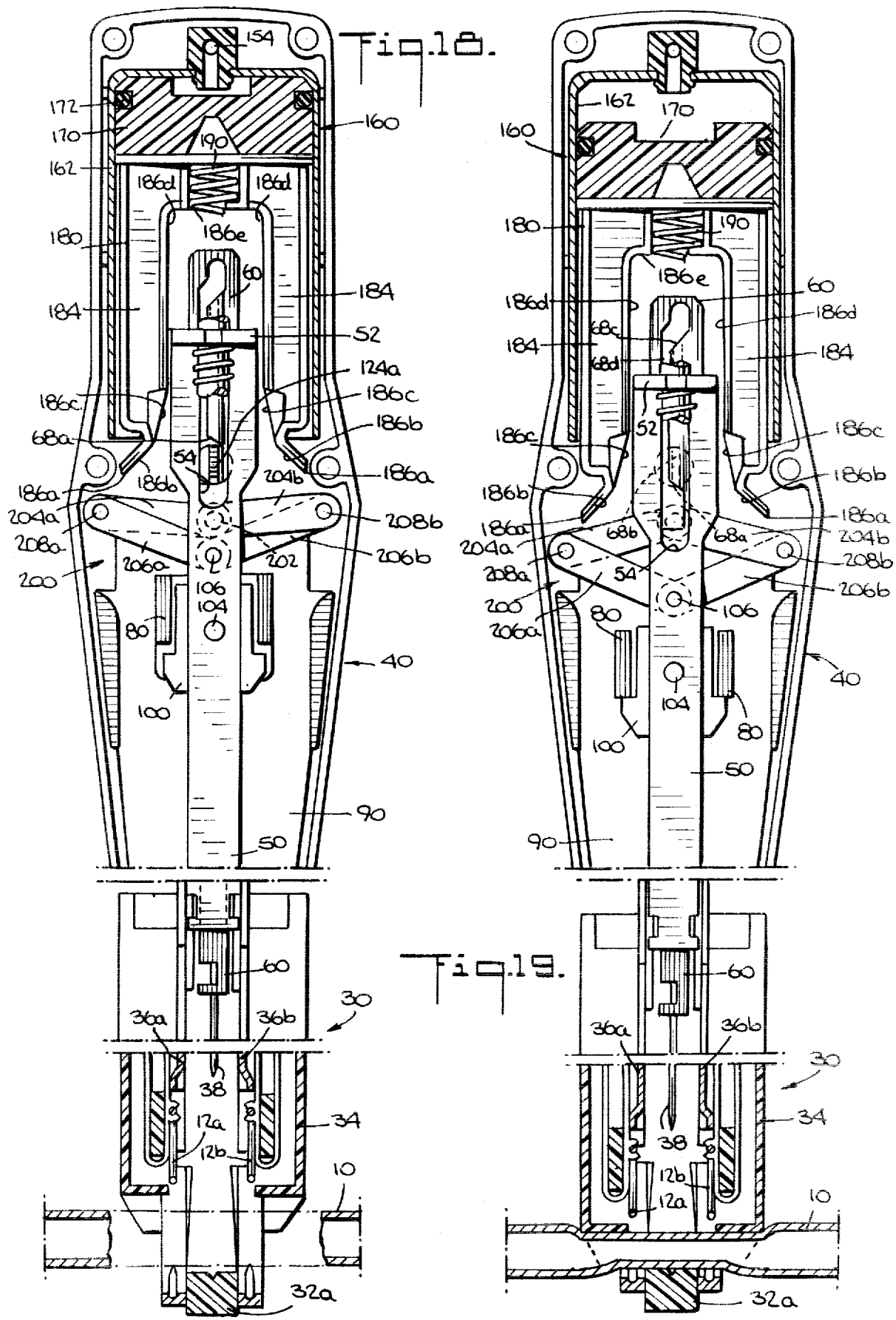

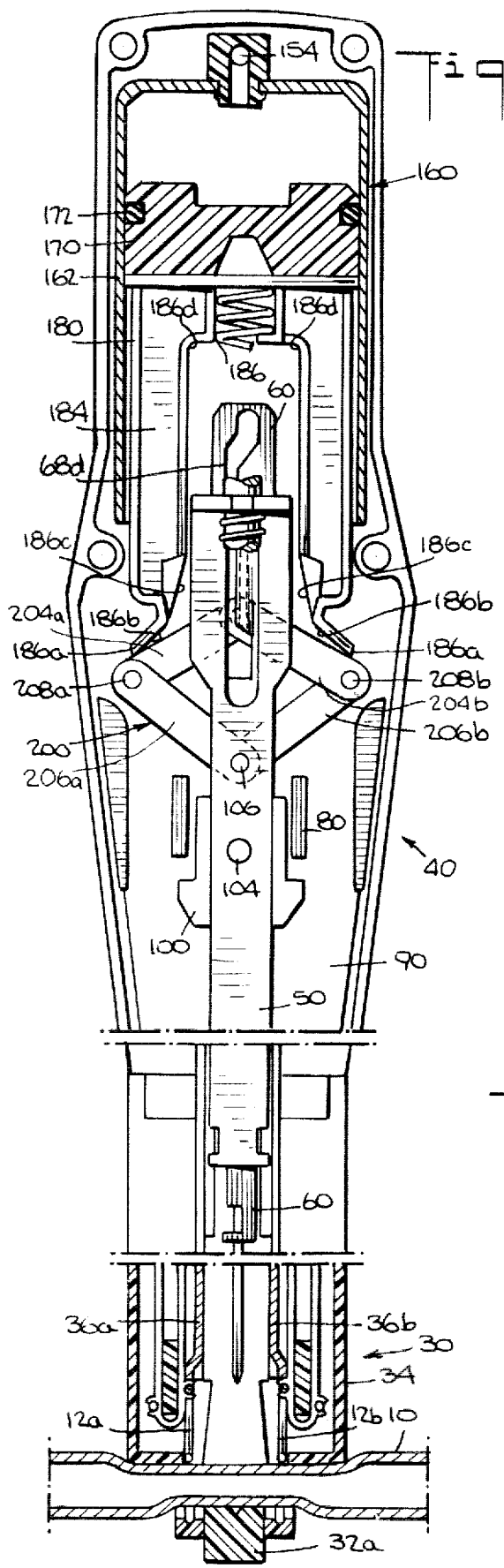
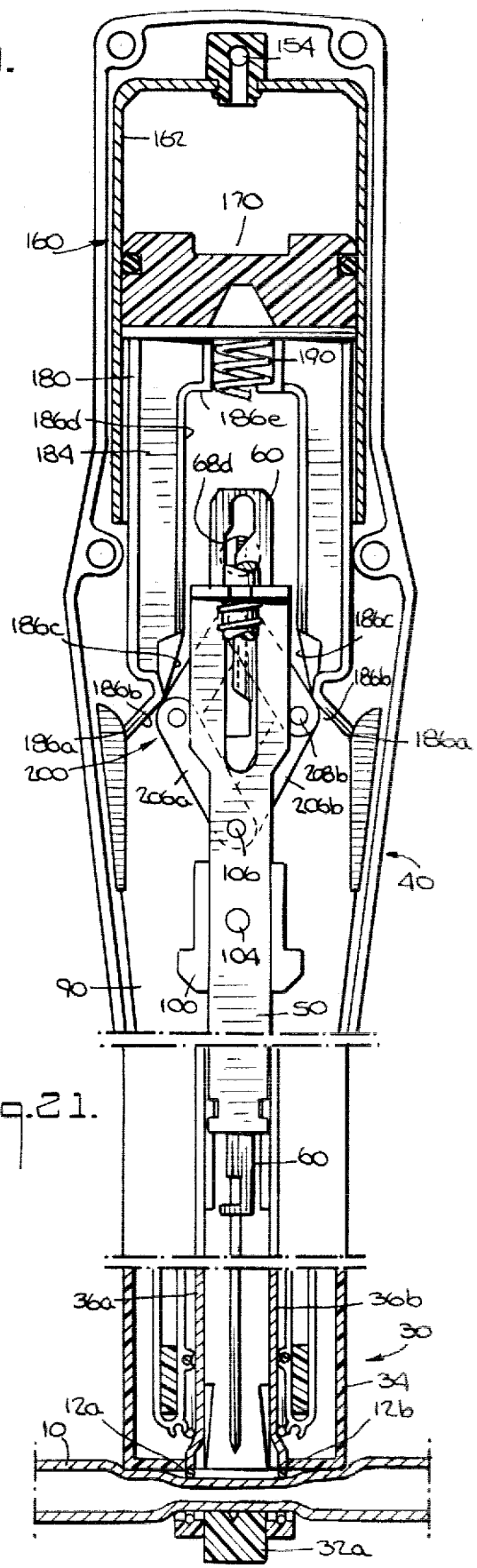
Fig. 20.
Fig. 21.

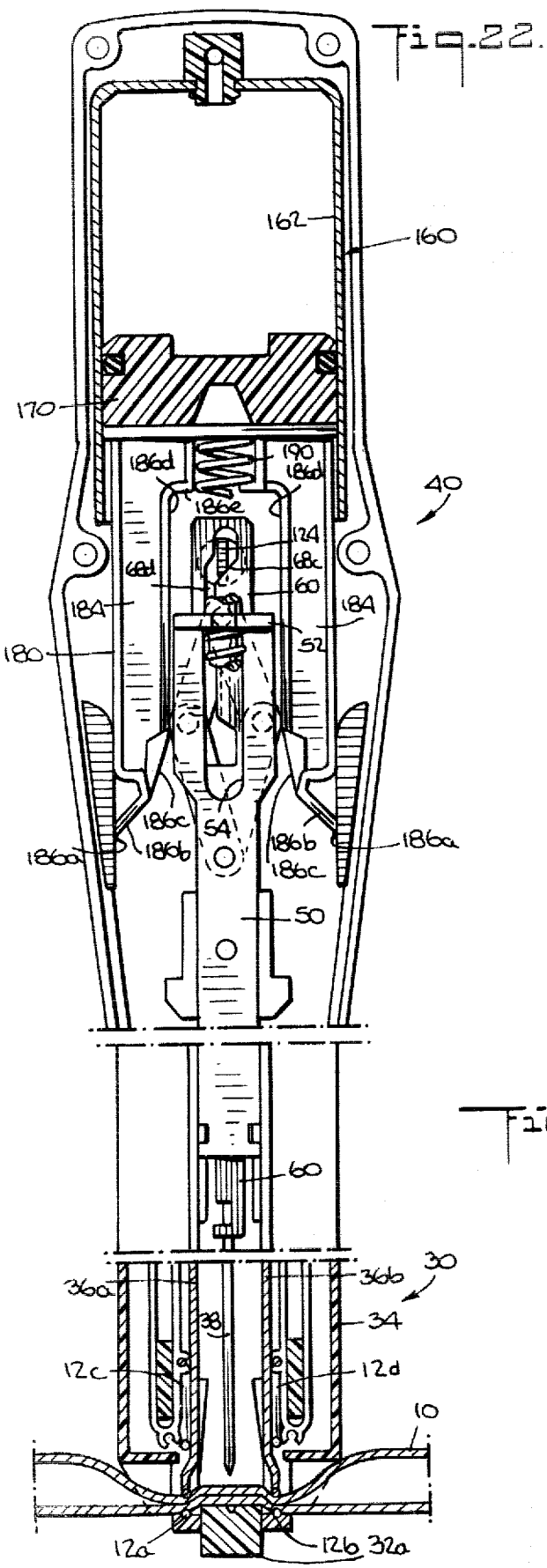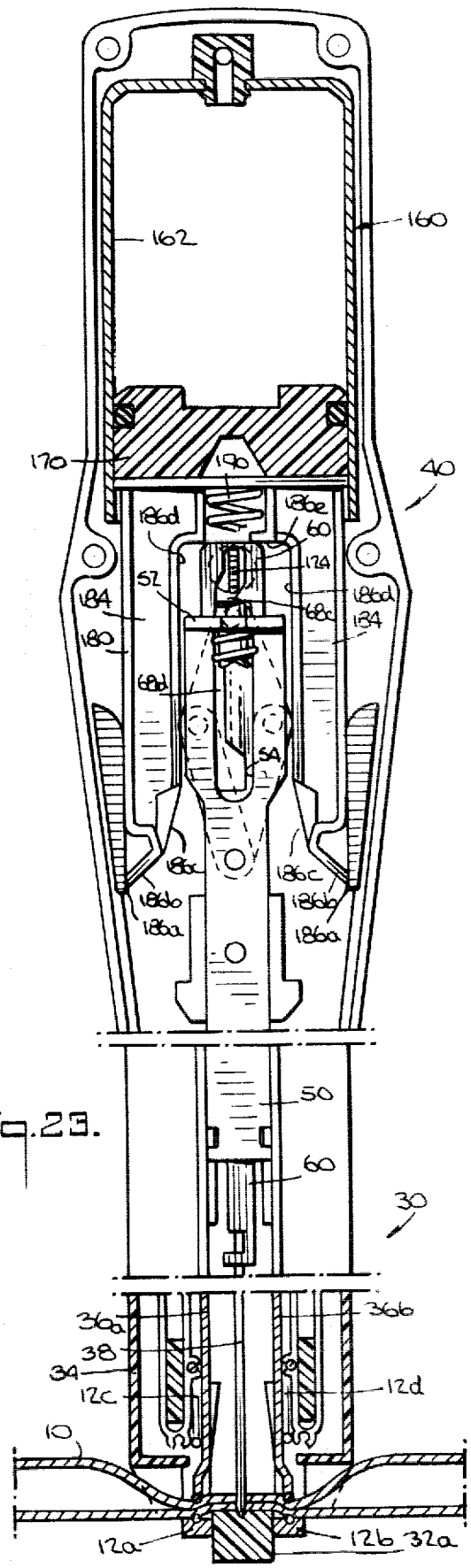
Fig. 22.
Fig. 23.

SURGICAL STAPLING APPARATUS HAVING SELF-CONTAINED PNEUMATIC SYSTEM FOR COMPLETING MANUALLY INITIATED MOTION SEQUENCE

BACKGROUND OF THE INVENTION

This invention relates to surgical stapling apparatus, and more particularly to surgical stapling apparatus which is at least partly powered by a pneumatic system contained within the apparatus and which performs a sequence of operations such as tissue clamping, staple advancing, staple forming, and/or tissue cutting.

Surgical stapling apparatus is known in which tissue is first clamped, then fastened or ligated by means of staple-like metal fasteners or ligatures, and finally trimmed or cut by means of a knife prior to being released from the apparatus. Apparatus of this general nature includes ligating and dividing devices of the type shown, for example, in Noiles et al. U.S. Pat. No. 3,665,924 and Green et al. U.S. Pat. No. 4,086,926, and anastomosis devices of the type shown, for example, in Astafiev et al. U.S. Pat. No. 3,552,626.

Because of the difficulty and expense of cleaning and sterilizing surgical instruments between uses, there is increasing interest in and demand for instruments which are disposable after use in a single surgical procedure rather than permanent and reusable. And because of the greater convenience and ease of using self-powered instruments (i.e., instruments which are powered by a power supply contained within the instrument, as opposed to manually powered instruments or instruments which are powered by an external power supply such as a large free-standing cylinder of compressed gas connected to the instrument by a length of pressure hose), as well as the more uniform results typically produced by self-powered instruments (as compared especially to manually powered instruments), there is increasing interest in and demand for instruments which are self-powered or at least partly self-powered.

Heretofore, these two demands have been somewhat conflicting as applied to surgical stapling apparatus like that mentioned above. The relatively large forces required to clamp tissue, to cut tissue, and especially to drive staple-like fasteners or ligatures seemed to necessitate either a relatively high pressure gas supply such as carbon dioxide (vapor pressure approximately 800 p.s.i.g. at room temperature), or a relatively large pneumatic actuator. High pressure gas is difficult to work with in an instrument designed to be economically disposable and therefore preferably made of inexpensive materials in a relatively light construction. On the other hand, a large pneumatic actuator supplied with low pressure gas increases the size and bulk of the instrument, thereby increasing the amounts of material required to make the instrument and consequently increasing its cost. A large instrument may also be more difficult or even impossible to use in certain surgical procedures.

Another difficulty associated with low pressure pneumatic systems is that a low pressure gas supply of acceptably small size can store only a limited amount of energy. If a low pressure pneumatic system is to be used, it is important to utilize the limited energy stored in the gas supply of that system efficiently in order to provide an instrument with an economically acceptable life span prior to exhaustion of the gas supply. Even if the instrument is made so that the gas supply can be replaced, it is desirable to minimize the frequency with which this is required. Efficient use of the gas supply is especially difficult in an instrument for performing several functions such as tissue clamping, staple advancing, staple forming, and tissue cutting because different amounts of force are typically required to perform each function. If the pneumatic actuator is designed to produce the largest force required to perform any function, the actuator will generally be wasting considerable energy during performance of the other functions when less than that amount of force is required. This will substantially shorten the useful life of the gas supply.

Although it is desirable to perform most of the functions of the stapling apparatus automatically using the self-powering elements in the apparatus, it may also be desirable for the initial function to be at least partly manual. For example, if the initial function is tissue clamping, it is preferably initiated manually so that it can be performed slowly and precisely and the results inspected and corrected if necessary before the automatic self-powered portion of the operating sequence begins.

In view of the foregoing, it is an object of this invention to improve and simplify surgical stapling apparatus of the type which performs a sequence of functions and which is at least partly powered by a pneumatic system contained within the apparatus.

It is a more particular object of this invention to provide surgical stapling apparatus for performing a sequence of functions which is initiated manually and which is thereafter powered by an efficiently utilized low pressure pneumatic system contained within the apparatus.

SUMMARY OF THE INVENTION

These and other objects of the invention are accomplished in accordance with the principles of the invention by providing surgical stapling apparatus in which the initial function (typically tissue clamping) is initiated by manual operation of the apparatus, after which the further functions of the apparatus are powered by a low pressure pneumatic system contained within the apparatus. The pneumatic system includes a low pressure gas supply and a pneumatic actuator. The pneumatic actuator is connected to the driven parts of the apparatus by a mechanical linkage which matches the force available from the pneumatic actuator throughout its stroke to the different amounts of force required to perform the several pneumatically powered functions. The pneumatic actuator can therefore be relatively small and the energy of the gas supply is used very efficiently.

Further features of the invention, its nature and various advantages will be more apparent from the accompanying drawing and the following detailed description of the invention.

BRIEF DESCRIPTION OF THE DRAWING

FIGS. 3–6 are exploded perspective views of various portions of the apparatus of FIG. 1.

FIGS. 7 and 8 are perspective views of portions of the apparatus of FIG. 1 showing that apparatus at two successive points in the normal operating cycle.

FIG. 9 is an elevational sectional view of part of the apparatus of FIG. 1 showing the initial condition of the apparatus.

FIGS. 10-13 and 16 are views similar to FIG. 9 illustrating the normal sequence of operation of the apparatus.

FIGS. 14 and 15 are detailed perspective views of portions of the apparatus of FIG. 1 illustrating the normal operation of those portions of the apparatus.

FIG. 18 is a view taken perpendicular to the view in FIG. 9 and parallel to the longitudinal axis of the apparatus showing the initial condition of the apparatus.

FIGS. 19-23 are views similar to FIG. 18 illustrating the normal sequence of operation of the apparatus.

DETAILED DESCRIPTION OF THE INVENTION

Although the principles of the invention are applicable to other types of surgical stapling instruments such as the thoracic-abdominal surgical staplers shown, for example, in Green et al. U.S. Pat. No. 3,494,533 and the anastomosis surgical staplers shown, for example, in Astafiev et al. U.S. Pat. No. 3,552,626, the invention will be fully understood from an explanation of its application to ligating and dividing instruments of the type shown, for example, in Noiles et al. U.S. Pat. No. 3,665,924 and Green et al. U.S. Pat. No. 4,086,926.

I. Overall Construction and Operation

As best seen in FIGS. 18-23, a ligating and dividing instrument places two spaced ligatures 12a and 12b, respectively, in or around body tissue 10 such as a blood vessel and then cuts through the tissue between the ligatures. In this way the tissue is severed, but the two severed ends of the tissue are both closed off by ligatures to prevent loss of body fluid (e.g., blood) from the tissue. Ligatures 12a and 12b are typically metal wire similar to surgical staples. The term "staple" as used herein will therefore be understood to include ligatures like ligatures 12a and 12b, and the term "surgical stapling apparatus" will be understood to include ligating and dividing apparatus of the type described herein, as well as other types of surgical stapling apparatus as mentioned above.

Figure 1:
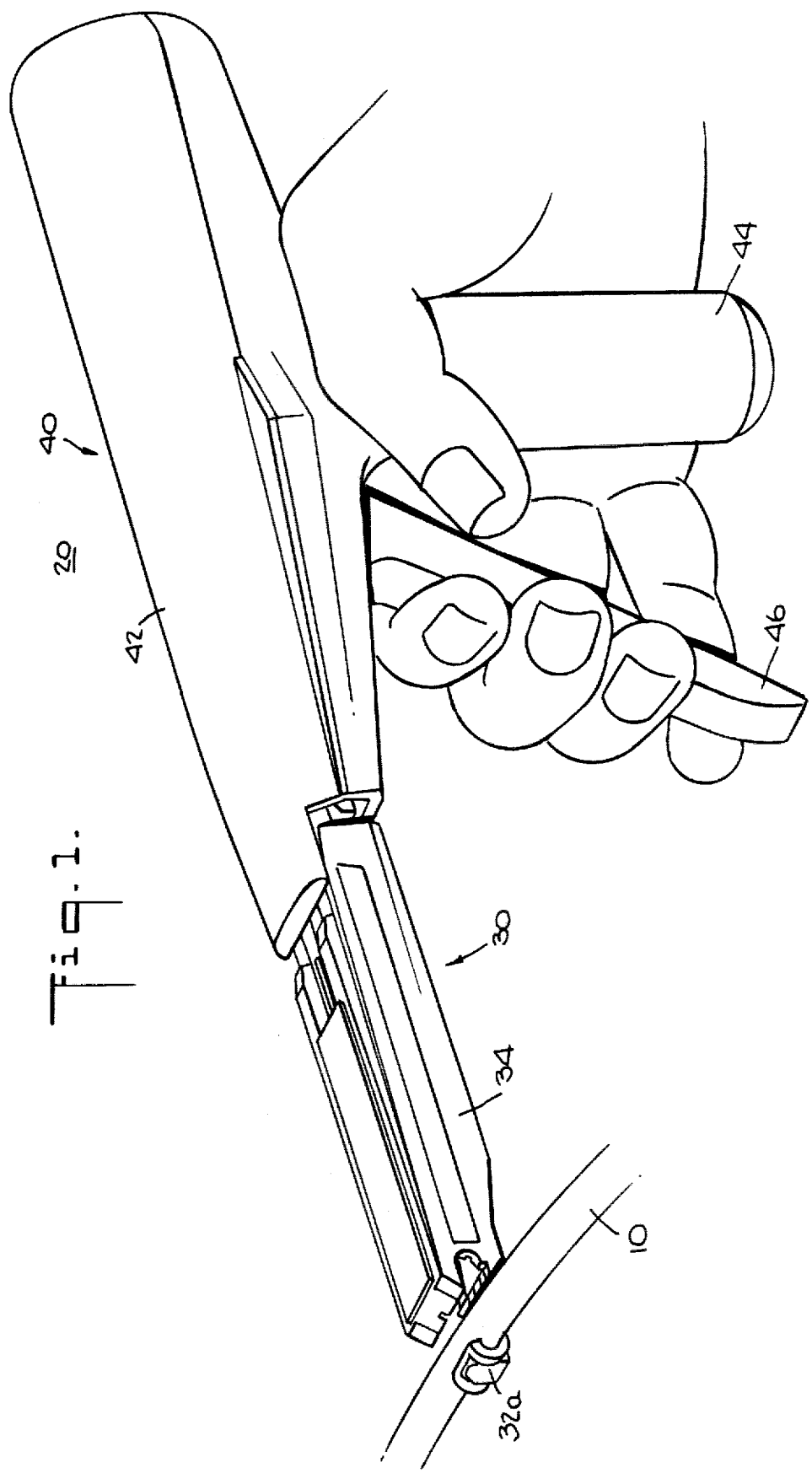
FIG. 1 is a perspective view of an illustrative embodiment of the invention.

As shown, for example, in FIG. 1, illustrative ligating and dividing apparatus 20 has two major components. There are an assembly 30 for actually performing the ligating and dividing procedure and an actuator 40 for actuating assembly 30. Assembly 30 may be similar to the ligating and dividing assembly shown, for example, in Green et al. U.S. Pat. No. 4,086,926, and reference can be made to that patent for a detailed explanation of the construction and operation of this assembly. Only such aspects of assembly 30 as are believed helpful for a ready understanding of the present invention will be referred to herein. In the case of apparatus 20 intended to be completely discarded after use in a single surgical procedure or after the supply of ligatures 12 in assembly 30 has been exhausted, whichever comes first, assembly 30 may be permanently mounted in the distal end of actuator 40 to prevent reloading and reuse of an instrument designed to be disposable. Alternatively, assembly 30 may be made as a cartridge removably mounted in the distal end of actuator 40 if actuator 40 is designed to be reloaded when the supply of ligatures in assembly 30 is exhausted.

Actuator 40 includes a longitudinal barrel portion 42 with a cylindrical handle portion 44 projecting transversely from a central portion of barrel 42. An actuator lever 46 also projects transversely from barrel 42 on the distal side of handle 44 so that lever 46 can be engaged by the fingers of the hand holding handle 44. Lever 46 is pivotally mounted in barrel 42 so that it can be pivoted toward or away from handle 44.

Assembly 30 includes a proximally extending support bar 32 (FIG. 2) which extends into the distal end of actuator 40 for attaching assembly 30 to actuator 40 either permanently or removably as described above. Support bar 32 is fixed relative to actuator 40 and extends along the bottom of assembly 30 as viewed in FIG. 1. Support bar 32 terminates at the distal end of the apparatus in anvil assembly 32a. Because anvil assembly 32a is part of support bar 32, anvil assembly 32a is also fixed relative to actuator 40. The remainder of assembly 30 is mounted on support bar 32 for reciprocal motion along the support bar.

Assembly 30 is actually operated by two actuator bars 50 and 60 (FIG. 2) which extend into the proximal end of assembly 30 and engage elements in that assembly as described in more detail below. In response to distal motion of actuator bar 50, all of assembly 30 other than support bar 32 translates distally along support bar 32 until the tissue 10 to be ligated and divided is clamped between the distal end of the outer housing 34 of assembly 30 and anvil assembly 32a (see FIG. 19). Thereafter, housing 34 remains stationary relative to support bar 32 and further distal motion of actuator bar 50 causes ligature pushers 36a and 36b (FIG. 19) to respectively advance ligatures 12a and 12b toward anvil assembly 32a. The ends of ligatures 12a and 12b pass around tissue 10 (FIGS. 7 and 8) and the ligatures are then crimped or crushed against the tissue by cooperation of the distal ends of ligature pushers 36a and 36b and the opposite portions of anvil assembly 32a. Ligating of the tissue is now complete and distal motion of actuator bar 50 stops.

During the above-described distal motion of actuator bar 50, actuator bar 60 also moves distally with bar 50. When the distal motion of actuator bar 50 stops, however, actuator bar 60 begins to move distally relative to bar 50. Actuator bar 60 is coupled to knife 38 (FIG. 19) in assembly 30. When actuator bar 50 stops moving, actuator bar 60 has carried the distal cutting end of knife 38 very near ligated tissue 10 (see FIG. 22). The further distal motion of actuator bar 60 forces the end of knife 38 through the tissue and against anvil assembly 32a, thereby cutting or dividing the ligated tissue.

When the tissue has thus been ligated and divided, actuator bars 50 and 60 both retract proximally. This retracts knife 38, ligature pushers 36a and 36b, and housing 34, thereby releasing the ligated and divided tissue from the apparatus. The distal ends of ligature pushers 36a and 36b fall back behind the next two ligatures 12c and 12d (FIGS. 22 and 23) in assembly 30 and the apparatus is then ready to begin another cycle of operation.

All of the above-described functions of the apparatus are initiated by operation of lever 46, i.e., by pivoting or squeezing lever 46 toward handle 44 as will now be described in more detail.

II. Detailed Construction

Figure 3:
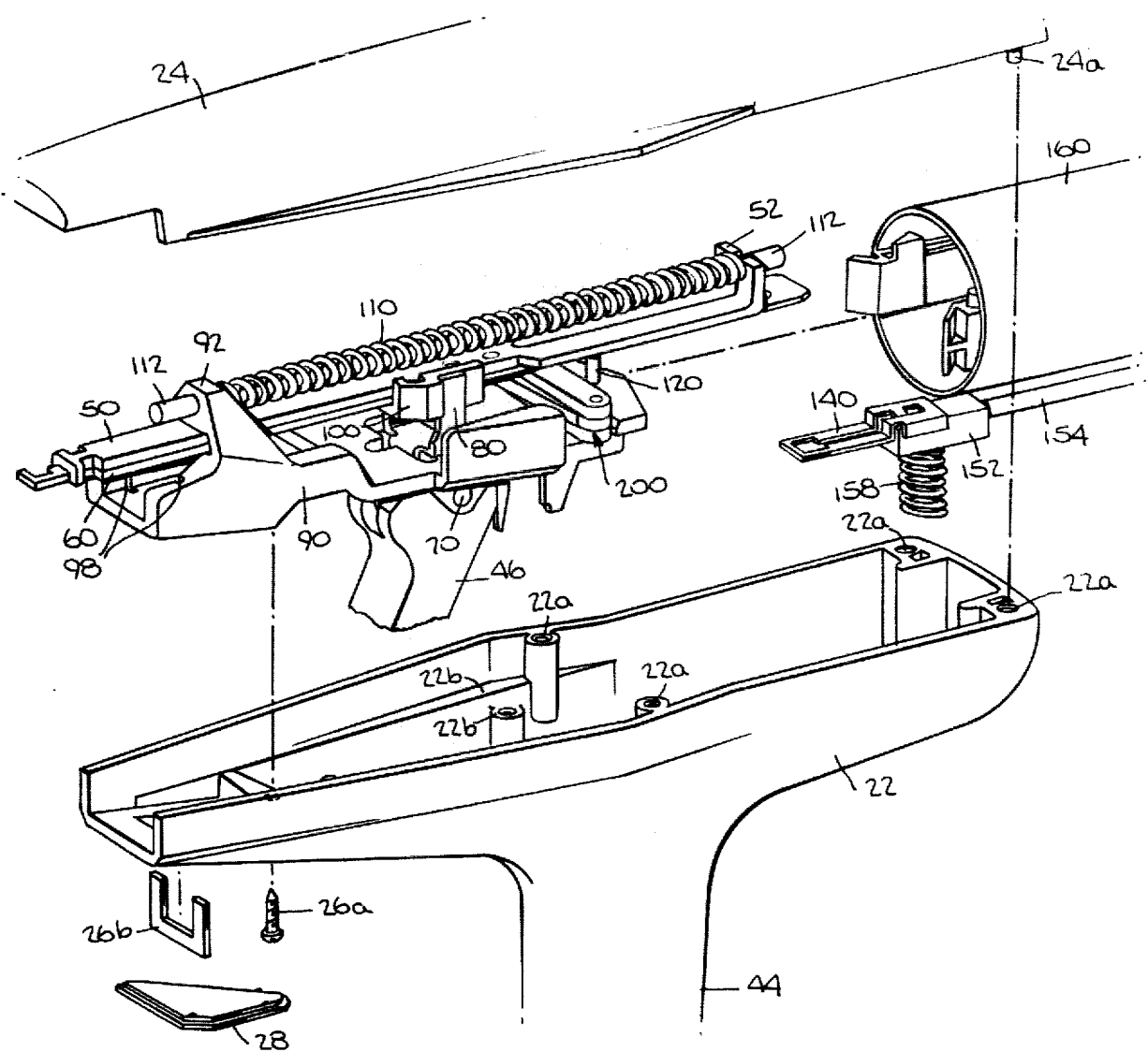

As shown in FIG. 3, the outer shell or housing of actuator 40 is made in two major portions: a lower portion 22 and an upper portion 24. These portions are aligned relative to one another by interfitting pegs 24a and holes 22a in the two respective portions, and are held together by any conventional means such as adhesive. Support member 90, which as described in detail below supports lever 46 and several other elements in the apparatus, is mounted in lower housing portion 22 by screw 26a threaded up through lower housing portion 22 into the support member (see also FIG. 9). Support member 90 is also supported in lower housing portion 22 by bearing on other shoulders 22b in the lower housing portion, and is also retained in the apparatus by U-shaped key 26b which projects through lower housing portion 22 into slots 98 in the distal end of support member 90. The head of screw 26a and the base of U-shaped key 26b are normally covered by cover plate 28 which fits into a corresponding aperture in lower housing portion 22 (see also FIG. 9).

As mentioned above, lever 46 directly controls the first portion of the distal motion of actuator bars 50 and 60. Thereafter, the apparatus becomes completely self-powered and the remainder of the distal motion of actuator bars 50 and 60 is powered by a pneumatic system in actuator 40. The return stroke is powered by return springs also located in actuator 40.

Figure 2:
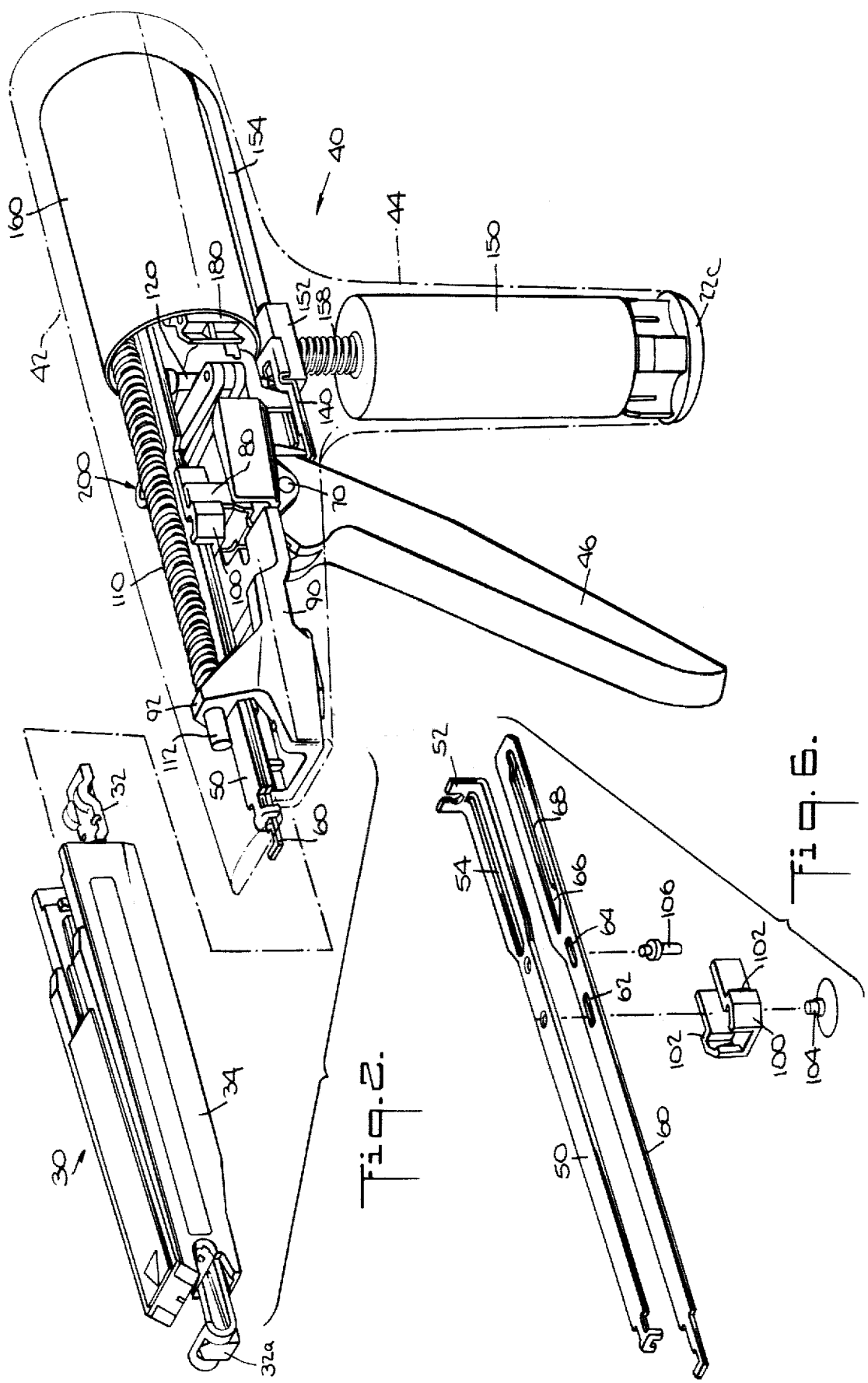
FIG. 2 is an exploded perspective view of the apparatus of FIG. 1 with a portion of the housing removed.

FIG. 2 shows the interior of actuator 40. Lever 46 is pivotally mounted on support member 90 by means of pivotal axis 70. The upper end of lever 46 (above axis 70 as viewed in FIG. 2) is connected to yoke 80 (see also FIG. 5) which extends up through support member 90 to normally contact transverse surfaces 102 on saddle 100 (see also FIG. 6). If desired, a light spring (not shown) may be provided to operate on lever 46 to normally bias the lever against saddle 100. Saddle 100 is connected to actuator bar 50 by pin 104 (FIG. 6) which passes through elongated slot 62 in actuator bar 60.

Actuator bar 60 is mounted for limited reciprocal motion relative to actuator bar 50 as is necessary to allow actuator bar 60 to drive knife 38 through the ligated tissue after actuator bar 50 has stopped moving in the distal direction. If desired, a light spring connection (not shown) may be provided between actuator bars 50 and 60 to normally maintain actuator bar 60 in its most proximal position relative to actuator bar 50. The distal end of elongated aperture 62 cooperates with pin 104 to move actuator bar 60 distally with actuator bar 50 during the forward stroke of actuator bar 50. Thereafter, elongated aperture 62 allows actuator bar 60 to be driven further forward relative to actuator bar 50 without disturbing actuator bar 50. During the return stroke of actuator bar 50, the proximal end of elongated aperture 62 cooperates with pin 104 to cause actuator bar 60 to return with actuator bar 50.

Actuator bars 50 and 60 are supported near their distal ends by passing through slot 92a (FIG. 5) in the upstanding distal end portion 92 of support member 90. Actuator bar 50 is supported near its proximal end by pin 106 (FIG. 6), which at its upper end passes through elongated aperture 64 in actuator bar 60 and into actuator bar 50, and which at its lower end is the forward-most connecting pin of the four bar linkage 200 (FIG. 2) which forms part of the mechanical linkage between the pneumatic system and the actuator bars (see also FIG. 19). Pin 106 not only supports the proximal end of actuator bar 50, but also provides the connection between that bar and four bar linkage 200. The proximal end of actuator bar 60 is supported from actuator bar 50 by saddle 100. Elongated aperture 64 is similar to aperture 62 and cooperates with pin 106 in the same way that aperture 62 cooperates with pin 104.

Actuator bar 50 is biased proximally by compression coil return spring 110 (FIG. 3) which extends between the upturned proximal end 52 of actuator bar 50 and the distal portion 92 of support member 90. Spring 110 is supported by pin 112 (FIG. 5) which passes through the center of spring 110. Pin 112 is attached to actuator bar 50 near its proximal end 52 and is slidably supported near its distal end by passing through aperture 92b (FIG. 5) in support member portion 92. The proximal bias of actuator bar 50 provided by return spring 110 is coupled to lever 46 by saddle 100 and yoke 80 and tends to normally pivot lever 46 clockwise as viewed in FIG. 2. The normal rest position of lever 46 is established by contact of lever surface 116 (FIG. 9) with surface 118 on the actuator housing.

Near the proximal end of support member 90, four bar linkage 200 is connected to support member 90 by the lower end of its rearmost connecting pin 202 (FIG. 5) which is mounted in support member aperture 94. Proximally of aperture 94, cam follower pin 120 (FIG. 5) is mounted for vertical reciprocation in support member aperture 96. Cam follower pin 120 is normally biased upward by compression coil spring 130 (FIG. 5) between shoulder 122 on pin 120 and the upper surface of support member 90. In the initial position of actuator bars 50 and 60 as shown, for example, in FIG. 9, the uppermost portion 124 of cam follower pin 120 projects through the distal end portion of elongated cam slot 66 (FIG. 6) in actuator bar 60 and into the distal end portion of elongated slot 54 in actuator bar 50. The upward motion of cam follower pin 120 is stopped by contact of the upper surface of shoulder 122 with the lower surface of actuator bar 60. Pin 120 passes through support member 90 and the lower end 126 of the pin bears on saddle portion 142 (FIG. 4) of member 140 (see also FIG. 8). Member 140 is mounted on actuator 152 (FIG. 2) of gas supply 150. When pin 120 is depressed as described below, it depresses gas supply actuator 152 and causes relatively low pressure gas to be dispensed from supply 150. This gas is conveyed to pneumatic actuator 160 via conduit 154. Pneumatic actuator 160 provides the power for driving actuator bars 50 and 60 through most of their forward stroke. Accordingly, cam follower pin 120 is the element principally responsible for controlling the pneumatic system in the apparatus.

As best seen in FIGS. 2 and 9, gas supply 150 is a cylindrical container located in handle 44 of actuator 40. Gas supply 150 is held in place in handle 44 by a closure member 22c (FIG. 3) which fits securely into the bottom of lower housing portion 22. The pressure of the gas in gas supply 150 during operation of the apparatus is typically less than 200 p.s.i.g., preferably in the range from about 30 p.s.i.g. to about 100 p.s.i.g., and most preferably in the range from about 40 p.s.i.g. to about 80 p.s.i.g. Any suitable non-toxic gas can be used. Suitable gases include halogenated hydrocarbons which are gaseous at room temperature, e.g., fluorinated hydrocarbons such as Freon 12 or chlorinated hydrocarbons such as Freon 152A. Gas supply 150 has an aerosol-type valve (not shown) for releasing gas from the container when hollow stem 156 on the top of the container is depressed. Actuator 152 is normally held off the upper end of stem 156 as shown in FIG. 9 by compression coil spring 158 between actuator 152 and the top of container 150. Accordingly, conduit 154 and pneumatic actuator 160 are normally vented to the atmosphere via the annular passage between actuator 152 and stem 156. When actuator 152 is depressed by cam follower pin 120 as described below, actuator 152 first seals the passage around stem 156 and then depresses the stem to dispense gas from container 150 (see FIG. 10).

As best seen in FIGS. 4 and 9, pneumatic actuator 160 comprises cylinder 162 disposed in the proximal end of actuator barrel 42. The proximal end of cylinder 162 is closed except for the connection to conduit 154. The distal end of cylinder 162 is open. Piston 170 is mounted in cylinder 162 for reciprocal motion parallel to the longitudinal axis of the cylinder. Piston 170 is pneumatically sealed to cylinder 162 by an O ring seal 172 carried by the piston.

As is also best seen in FIGS. 4 and 9, yoke 180 is mounted on the distal side of piston 170. Yoke 180 has a base 182 adjacent piston 170 and two spaced arms 184 extending distally from the base. The inner surface 186 of yoke 180 cooperates with four bar linkage 200 (FIG. 5) in the manner of a wedge or cam surface to transmit the power of pneumatic actuator 160 to actuator bars 50 and 60 with varying degrees of mechanical advantage as is required to match the force available from the pneumatic actuator to the force required during various portions of the forward stroke of the apparatus.

The shape of the operative surface 186 of yoke 180 is best seen in Figures like FIG. 18. Immediately adjacent the extreme distal ends 186a of arms 184 are first synclinal surface portions 186b. These surface portions are inclined toward one another in the proximal direction and form relatively large, equal and opposite, acute angles with the longitudinal axis of the apparatus. Adjacent surface portions 186b in the proximal direction are second synclinal surface portions 186c. These surface portions are also inclined toward one another in the proximal direction, but form somewhat smaller, equal and opposite, acute angles with the longitudinal axis of the apparatus. Adjacent surface portions 186c in the proximal direction are substantially parallel surface portions 186d. The final portion of operative surface 186 is surface portion 186e which is substantially perpendicular to the longitudinal axis of the apparatus at the proximal end of surface portions 186d.

Yoke 180 and piston 170 are normally biased against the proximal end of cylinder 162 as shown, for example, in FIG. 9 by compression coil piston return spring 190 which extends between yoke 180 and the proximal surface of the upturned end 52 of actuator bar 50. Piston return spring 190 always exerts substantially less force than main return spring 110 so that it does not overcome the proximal bias of actuator bar 50 due to spring 110.

The final element to be described is four bar linkage 200, which as mentioned above cooperates with yoke 180 to apply the force produced by pneumatic actuator 160 to actuator bar 50 with varying mechanical advantage. As shown, for example, in FIG. 5, four bar linkage 200 has two proximal links 204a and 204b of equal length pivotally connected to one another and to support member 90 by pin 202. Linkage 200 also has two distal links 206a and 206b of equal length pivotally connected to one another and to actuator bar 50 by pin 106. Links 204a and 206a are pivotally connected to one another by pin 208a, and links 204b and 206b are similarly connected to one another by pin 208b. As shown, for example in FIGS. 2 and 18, four bar linkage 200 is located distally of yoke 180 so that yoke 180 can operate on the proximal legs of linkage 200 adjacent pins 208a and 208b as described in more detail below.

III. Normal Operation

Normal operation of the apparatus begins with actuator 40 in the condition shown in FIGS. 9 and 18. Lever 46 is normally located away from handle 44 in the position shown in FIG. 9. Actuator bar 50 is in its rearmost position. Piston 170 is against the proximal end of cylinder 162. Actuator bar 60 is also in its rearmost position. This allows cam follower pin 120 to assume its uppermost position with portion 124 projecting up through the extreme distal end of cam slot 66 into longitudinal slot 54. The tissue 10 to be ligated and divided is positioned in the apparatus between anvil assembly 32a and the distal end of housing 34 as shown in FIGS. 1 and 18.

A cycle of operation is initiated by squeezing lever 46 toward handle 44. Yoke 80 pivots counterclockwise with lever 46 and, in cooperation with saddle 100, immediately begins to translate actuator bar 50 in the distal direction. This immediately begins to translate housing 34 in the distal direction toward anvil assembly 32a, thereby initiating clamping of the tissue between the distal end of housing 34 and anvil assembly 32a. Pins 104 and 106 (FIG. 6) cooperate with the distal ends of elongated apertures 62 and 64 in actuator bar 60 to translate actuator bar 60 with actuator bar 50. After an initial segment of forward motion, the leading edge 68a (FIG. 18) of cam surface 68 on actuator bar 60 contacts the inclined surface 124a (FIG. 9) on the top of cam follower pin 120 (see also FIG. 7). Further forward motion of actuator bars 50 and 60 causes cam surface portion 68a to gradually depress cam follower pin 120 until the top surface 124b enters longitudinal groove 68b in the lower surface of cam 68 as shown in FIGS. 7 and 10. When cam follower pin 120 is thus fully depressed, gas supply actuator 152 contacts and depresses stem 156 on gas supply container 150 as shown in FIG. 10, thereby dispensing gas from the container through conduit 154 to pneumatic actuator cylinder 162 behind piston 170. At this point the pneumatic system of the apparatus takes over the manually operated lever 46 to continue the operating cycle of the apparatus.

The apparatus is preferably designed so that the first few degrees of pivoting of lever 46 provide at least an initial portion of the clamping of the tissue between anvil assembly 32a and housing 34 without initiating operation of the pneumatic system. At least this portion of the pivoting of lever 46 is also preferably reversible. In this way the operator of the instrument can position the instrument around the tissue to be ligated and divided and manually test the clamping of the tissue without triggering the pneumatic system and thereby committing the apparatus to a full cycle of operation. Lever 46 is also preferably pivotable only far enough to cause cam follower pin 120 to be fully depressed as shown in FIG. 10 to initiate the pneumatically powered portion of the operating cycle. Lever 46 is not pivotable so far that the upper end of yoke 80 falls below the line of travel of saddle 100. Lever 46 may come to rest against handle 44 or may be stopped by contact of upper portions of the lever with adjacent portions of support member 90.

As pressurized gas from container 150 begins to flow into pneumatic actuator 160, it begins to drive piston 170 in the distal or forward direction as shown in FIGS. 11 and 19. Piston 170 drives yoke 180 in the same direction, thereby slightly compressing spring 190 until the extreme distal end surfaces 186a of yoke 180 contact the proximal links 204a and 204b of four bar linkage 200 near pins 208a and 208b as best seen in FIG. 20. At that point, further forward motion of piston 170 and yoke 180 causes links 204a and 204b to pivot toward one another about fixed pin 202. This causes four bar linkage 200 to extend along the longitudinal axis of the apparatus so that pin 106, which connects links 206a, 206b and actuator bar 50, is driven in the distal direction by the mechanical linkage including yoke 180 and four bar linkage 200. The forward motion of actuator bars 50 and 60 is thus resumed under power of pneumatic actuator 160.

During this phase of motion of the apparatus, the mechanical linkage including elements 180 and 200 amplifies the motion or displacement of piston 170. This is possible because relatively low force is required to complete the clamping of the tissue and advance ligatures 12a and 12b toward the tissue, as occurs during this portion of the operating cycle of the apparatus. As actuator bars 50 and 60 continue to move forward, cam follower surface 124b on pin 120 follows longitudinal cam surface 68b on actuator blade 60. This keeps pin 120 and gas supply actuator 152 depressed and thereby maintains the flow of pressurized gas from container 150 to pneumatic actuator 160. Piston 170 and yoke 180 therefore continue to advance in the distal direction.

As yoke 180 continues to advance and four bar linkage 200 continues to extend, the mechanical advantage of the combination of yoke 180 and linkage 200 gradually changes from amplifying the displacement of pneumatic actuator piston 170 to amplifying the force produced by the pneumatic actuator. Thus initially the ends 186a of yoke 180 operate on proximal links 204a and 204b as described above to amplify the displacement of the pneumatic actuator. Thereafter, synclinal surfaces 186b and 186c operate in turn on four bar linkage 200 near pins 208a and 208b in a wedge-like manner as illustrated by FIG. 21 to continue the extension of four bar linkage 200, but at a substantially reduced rate compared to the rate of displacement of piston 170. Accordingly, the displacement of piston 170 is no longer amplified, but the force produced by the pneumatic actuator is considerably amplified as applied to actuator bar 50 through the mechanical linkage comprising yoke 180 and four bar linkage 200. The increase in force thus applied to actuator bar 50 coincides with the increase in force required to crimp or crush ligatures 12a and 12b around and against tissue 10 to ligate the tissue.

When ligatures 12a and 12b have been fully formed, four bar linkage 200 contacts parallel surfaces 186d of yoke 180 as best seen in FIG. 22. Accordingly, four bar linkage no longer continues to extend with further forward motion of piston 170 and yoke 180. The forward motion of actuator bar 50 therefore stops. Cam follower pin 120 continues to be depressed and pressurized gas accordingly continues to flow to pneumatic actuator 160. The forward motion of piston 170 therefore continues. After a further short motion of piston 170, the transverse surface 186e near the proximal end of yoke 180 contacts the proximal end of actuator bar 60. Actuator bar 60 is thus directly coupled to pneumatic actuator 160. Further forward motion of piston 170 therefore drives actuator bar 60 forward relative to actuator bar 50 and causes it to advance knife 38 through the ligated tissue as shown in FIG. 23. Actuator bar 60 can move forward relative to actuator bar 50 in this manner because of elongated apertures 62 and 64 in actuator bar 60.

The relationship between actuator bar 60 and cam follower pin 120 during the latter portions of the forward stroke of the apparatus is best seen in FIGS. 8, 12 and 13. As four bar linkage 200 contacts yoke surfaces 186d, cam follower surface 124b is nearing the proximal end 68c of cam surface 68b (FIGS. 8 and 12). After the further forward motion of actuator bar 60 required to cause knife 38 to divide the tissue as described above, cam follower surface 124b is released from the proximal end of cam surface 68b and pin 120 accordingly pops up so that the upper portion 124 of the pin projects through the proximal portion of cam slot 66 in actuator bar 60 as shown in FIG. 13 (see also FIG. 23). This releases gas supply actuator 152, stops the flow of pressurized gas from container 150, and vents pneumatic actuator 160 to the atmosphere via conduit 154 and the annular passage between actuator 152 and the top of container stem 156. This initiates the return stroke of the apparatus.

During the forward stroke of the apparatus, both main return spring 110 and piston return spring 190 are gradually compressed. When pneumatic actuator 160 is vented as described above, piston return spring 190 begins to push yoke 180 and piston 170 back in the proximal direction, and spring 110 similarly begins to push actuator bars 50 and 60 back in the same direction shown in FIG. 16. At the start of the return stroke, the transversely inclined cam surface 68c at the proximal end of cam 68 contacts vertical cam follower surface 124c and guides the upper portion of cam follower pin 120 into longitudinal return stroke cam slot 68d as shown in FIG. 14. Once in return stroke cam slot 68d, the upper portion of cam follower pin 120 follows that slot as shown in FIG. 15 throughout the entire return stroke of the apparatus. Cam follower pin 120 remains up throughout the return stroke, thereby allowing pneumatic actuator 160 to continue to vent. Springs 110 and 190 return all elements of the apparatus to their initial positions, thereby releasing the ligated and divided tissue from the apparatus and readying the apparatus for another cycle of operation when lever 46 is operated again.

If lever 46 has not been released by the operator when the apparatus nears the end of its return stroke, the return stroke is not completed until lever 46 is released. This is because pivoted yoke 80 contacts saddle 100 and prevents actuator bars 50 and 60 from fully returning to their initial positions. The apparatus cannot begin another cycle of operation until lever 46 has been released and the first cycle is completed because the upper portion of cam follower pin 120 does not leave the distal end of return stroke cam slot 68d and return to its initial position adjacent cam surface 68a until actuator bar 60 is back in its initial position.

The progressively increasing mechanical advantage provided by the mechanical linkage including yoke 180 and four bar linkage 200 during the forward stroke of the apparatus is important to the economical design and function of the apparatus. The resulting economies include the ability of the apparatus to provide the relatively large forces required to crimp or crush the metal ligatures with a relatively small pneumatic actuator 160 supplied with relatively low pressure gas, as well as the efficient use of the gas in the gas supply. These features of the apparatus are further illustrated in FIG. 24.

Figure 24:
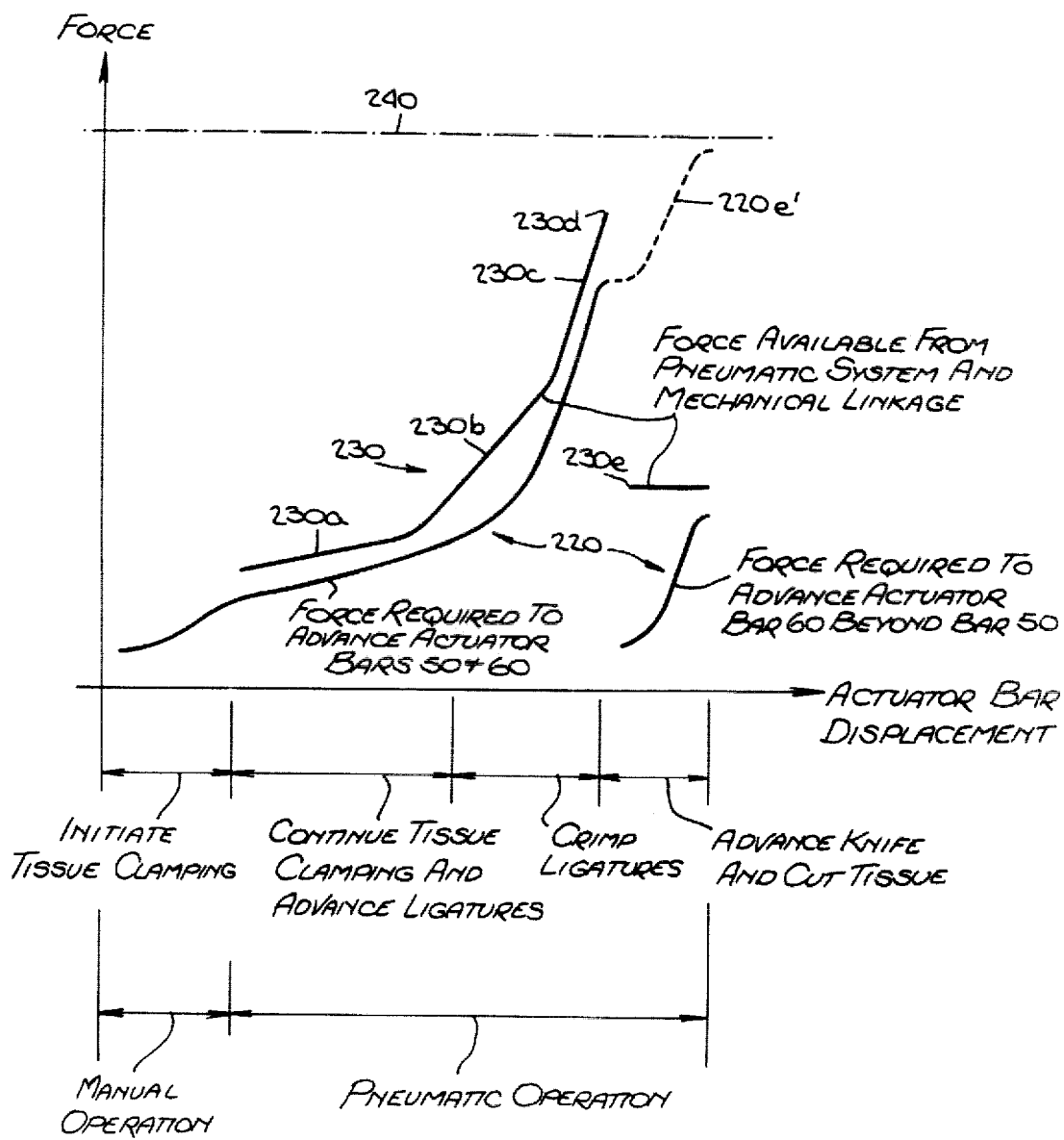
FIG. 24 is a diagram of force versus displacement which is useful in explaining the operation and advantages of the illustrative embodiment.

In FIG. 24 the force required to advance actuator bars 50 and 60 to perform the various functions of the apparatus is represented as a function of the displacement of those bars by curve 220. The force available from the pneumatic system and the mechanical linkage is represented as a function of the displacement of the actuator bars by curve 230. As shown by curve 220, the force required to advance actuator bars 50 and 60 is initially relatively low as the tissue is clamped and the ligatures are merely being advanced toward the tissue. As the apparatus begins to crimp the ligatures, however, the force required increases rapidly until the ligatures are fully crimped and the forward motion of actuator bar 50 stops. Thereafter, substantially smaller forces (as compared to the latter portion of the ligature crimping force) are required to advance actuator bar 60 and cut the tissue.

As can be seen in FIG. 24, the force available from the pneumatic system and mechanical linkage (curve 230) is always greater than, but closely follows, the force required to advance the actuator bars (curve 220). Thus, during the first portion of the pneumatic actuator stroke, when the distal ends 186a of yoke 180 operate on four bar linkage 200, the force available from the self-powering apparatus is relatively low (portion 230a of curve 230). The force available increases steeply as synclinal surfaces 186b operate on four bar linkage 200 (portion 230b of curve 230). This force increases even more steeply as synclinal surfaces 186c operate on the four bar linkage (portion 230c of curve 230). Finally, when parallel surfaces 186d contact four bar linkage 200, actuator bar 50 is effectively locked in place with no additional work from pneumatic actuator 160 being required to maintain that condition (point 230d on curve 230). All further pneumatic actuator force (portion 230e of curve 230) is used to overcome the friction between yoke surfaces 186d and the adjacent surfaces of four bar linkage 200 and to advance actuator bar 60 relative to actuator bar 50. The penumatic actuator force required to advance actuator bar 60 relative to actuator bar 50 is applied directly to the proximal end of actuator bar 60 by yoke surface 186e.

The varying available force described above is produced by the mechanical linkage (elements 180 and 200) from a substantially constant force exerted by pneumatic actuator 160 throughout its driving stroke. The constant force exerted by pneumatic actuator 160 is typically greater than the relatively low force required or available during the initial tissue clamping and ligature advancing portions of the stroke, but less than the relatively high force required or available during the final ligature crimping portions of the stroke. Preferably the pneumatic energy expended during each incremental advance of pneumatic piston 170 (given by the expression PdV, where P is the pressure of the gas supplied by gas supply 150 and dV is the corresponding incremental change in the volume enclosed by cylinder 162 and piston 170) is approximately equal to the mechanical work performed during the corresponding incremental advance of actuator bars 50 and/or 60 (given by the expression Fdx, where F is the force required to advance actuator bars 50 and/or 60 and dx is the corresponding incremental advance of the actuator or actuators). Accordingly, substantially all of the pneumatic energy expended in each stroke is converted to required mechanical work, and the available pneumatic energy is used very efficiently.

By way of contrast, if a direct pneumatic drive were used for the entire advance of actuator bars 50 and 60, the pneumatic actuator would have to be sized to provide the maximum force required throughout its entire stroke in order to meet that maximum force requirement when it occurred. (The maximum force would also probably be increased somewhat from that discussed above because the cutting force would probably be superimposed on the ligature crimping force as indicated by the broken line 220e' in FIG. 24.) If low pressure gas were used, this would necessitate a pneumatic actuator with a relatively large diameter. The curve of force available for such a device would be represented by broken line 240 in FIG. 24, and an amount of pneumatic energy proportional to the area between this line and the several portions of curve 230 would be wasted (as compared to the illustrative apparatus) during each driving stroke of the apparatus. Similarly, if an indirect drive with a constant value of mechanical advantage were used to make possible the use of a smaller diameter actuator with low pressure gas, the pneumatic actuator would have to be made much longer than the present actuator and the same amount of pneumatic energy would be wasted during each stroke.

Thus, the apparatus of this invention is capable of producing the relatively large forces required in a ligating and dividing procedure with a relatively small pneumatic actuator supplied with low pressure gas, while at the same time making efficient use of the gas supply. Although the following parameters may vary for different types of apparatus and specific values are mentioned here for purposes of illustration only, the maximum total force required to actuate assembly 30 is typically about 95 lbs. (which does not include the additional force of the return springs in actuator 40), the gas pressure is typically as given above, the piston area is typically about 1.09 square inches, and the stroke of the piston is typically about 1.16 times the aggregate displacement of actuator bars 50 and 60.

IV. The Interrupt Feature

The illustrative embodiment of the invention includes means for interrupting the normal operating cycle of the apparatus in the event that either assembly 30 or actuator 40 becomes jammed during such a cycle and it becomes necessary to remove the apparatus from the tissue. This interrupt apparatus operates by releasing gas supply actuator 152 from the downward pressure of cam follower pin 120, thereby allowing pneumatic actuator 160 to vent. This allows return springs 110 and 190 to return actuator bars 50 and 60 to their initial positions and thereby opens assembly 30 to release the tissue.

As described above, the lower end of cam follower pin 120 rests on a saddle 142 of member 140 (see, for example, FIG. 8). Proximally of saddle 142 member 140 has an aperture 144 large enough to pass the lower portion of pin 120. The portion 152a (FIG. 4) of gas supply actuator 152 below saddle 142 is cut away by an amount also large enough to receive the lower portion of pin 120. Member 140 fits snugly on dispenser actuator 152, but can be pulled in the distal direction relative to actuator 152 when it is desired to interrupt the operating cycle of the apparatus.

The distal end of member 140 includes an aperture 146 (FIG. 4) through which a downwardly extending finger 72 (FIG. 9) on the proximal side of lever 46 extends, at least when lever 46 is in the normal rest position.

Figure 17:
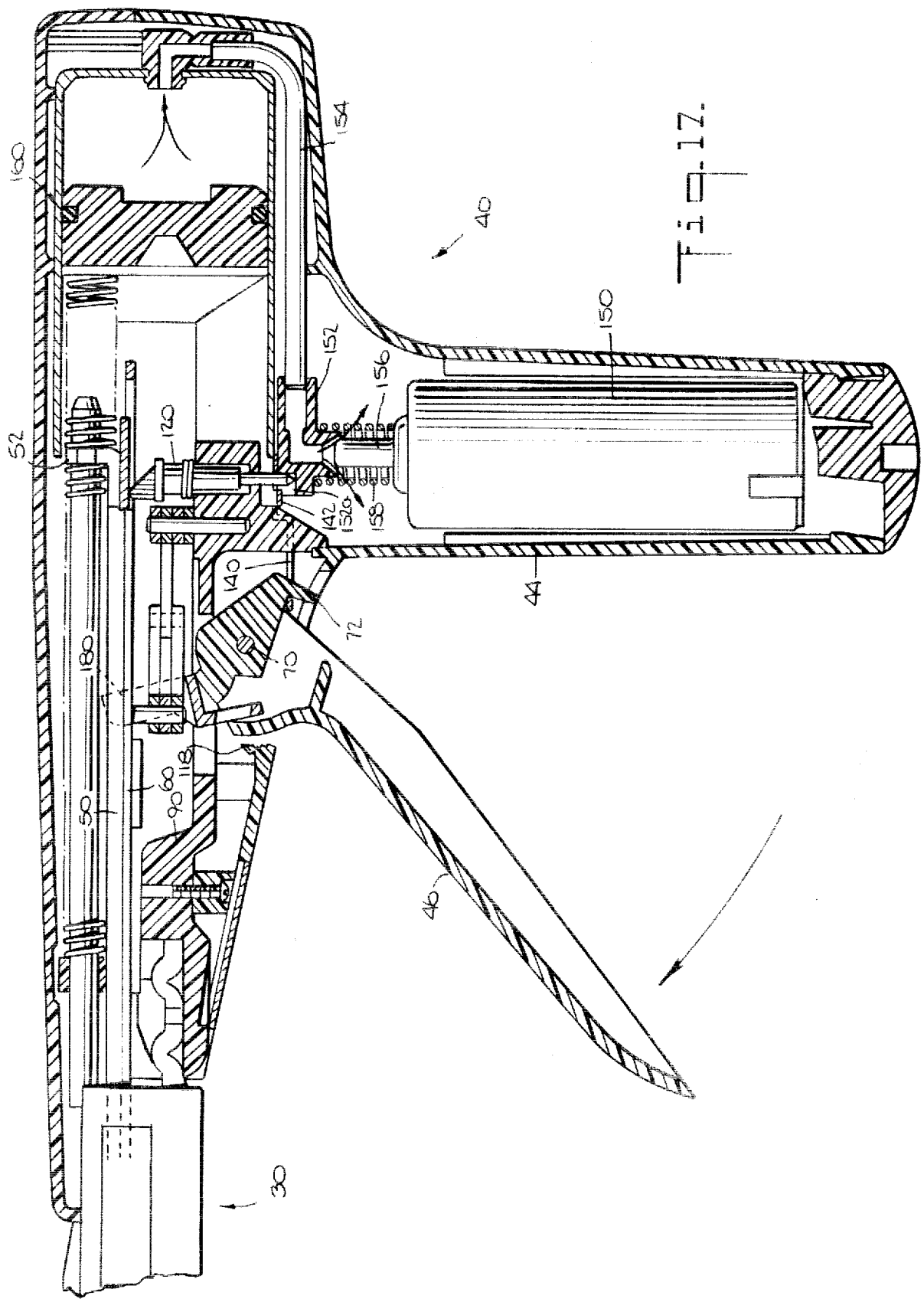
FIG. 17 is a view similar to FIG. 9 showing how the apparatus can be manipulated to interrupt the normal operating cycle.

If it is desired to interrupt the operating cycle of the apparatus, lever 46 is forcibly pivoted away from handle 44 past the normal rest position as shown in FIG. 17. This breaks the portion 118 of the actuator housing which normally stops the clockwise pivoting of lever 46 and causes finger 72 to pull member 140 distally relative to gas supply actuator 152. This pulls saddle 142 out from under pin 120 and exposes aperture 152a in gas supply actuator 152. Gas supply actuator 152 is thereby released from the downward pressure of pin 120 and can rise as shown in FIG. 17 to vent pneumatic actuator 160. This allows return springs 110 and 190 to return actuator bars 50 and 60 to their initial positions, thereby opening assembly 30 and releasing the tissue.

Operating the interrupt mechanism in the illustrative embodiment renders the apparatus incapable of further use because lever stop 118 is broken and there is no convenient way to restore member 140 to its original position. Accordingly, the interrupt feature in this embodiment is only intended for use under unusual circumstances such as when the apparatus is stalled or jammed and cannot otherwise be removed from the tissue.

V. Other Features

Because the apparatus makes use of relatively low pressure gas, it can be safely and economically made as a disposable item using inexpensive materials such as plastic for a large proportiom of its parts. For example, such elements as actuator housing portions 42 and 44, lever 46, yoke 80, support member 90, saddle 100, gas supply actuator 152, conduit 154, piston 170, yoke 180, and most of the parts of four bar linkage 200 can all be made of plastic. Only the relatively high stress elements such as actuator bars 50 and 60, pin 120, rod 112, container 150, cylinder 162, and the various connecting pins and springs need be made of metal. And because container 150 and cylinder 162 are exposed only to relatively low pressure gas, these elements can be made of relatively light construction such as relatively thin aluminum. All of these factors greatly reduce the cost of the apparatus and make it economical to produce as a disposable item. The extensive use of plastic and light weight metals also makes it easy to dispose of the apparatus by conventional techniques such as incineration and/or compaction.

The illustrative apparatus also has another feature which facilitates safe disposal, especially when high temperatures are involved such as in incineration. The bottom surface 150a (FIG. 9) of container 150 is normally curved inwardly (i.e., concave). Beneath container 150 is a metal plate or disc 210 (FIG. 3) having a sharply pointed spike 212 pointing upward toward the center of container surface 150a. If, during disposal of the apparatus (or at any other time during its life), the pressure in container 150 exceeds a predetermined threshold value, the concave surface 150a inverts (i.e., becomes convex). When this occurs, spike 212 pierces container surface 150a and allows the gas remaining in container 150 to escape harmlessly without a possibly hazardous explosion of the container.

It will be understood that the embodiments shown and described herein are merely illustrative of the principles of the invention, and that various modifications can be made by those skilled in the art without departing from the scope and spirit of the invention. For example, the overall shape of actuator 40 could be very different from the particular shape shown herein.

I claim:

1. In apparatus for ligating and dividing body tissue including first means for clamping the tissue in the apparatus and then advancing two spaced staple-like metal ligatures toward the clamped tissue and crimping the ligatures around the tissue, and second means for cutting the tissue between the crimped ligatures, an actuator comprising:
    a first movably mounted actuator member for actuating the first means;
    a second movably mounted actuator member for actuating the second means;
    a pneumatic system including a supply of pressurized gas pneumatically connected to a pneumatic actuator;
    a first mechanical linkage for connecting the pneumatic actuator to the first actuator member for moving the first actuator member to actuate the first means during an initial first part of the power stroke of the pneumatic actuator and for holding the first actuator member stationary during a subsequent second part of the power stroke of the pneumatic actuator;
    a second mechanical linkage for connecting the pneumatic actuator to the second actuator member for moving the second actuator member relative to the first actuator member to actuate the second means during the second part of the power stroke of the pneumatic actuator;
    manually operable means mechanically connected to the first actuator member for initiating motion of the first actuator member to at least initiate clamping of the tissue by the first means; and
    means responsive to a predetermined manually produced motion of the first actuator member beyond the motion which at least initiates clamping of the tissue by the first means for releasing pressurized gas from the gas supply to initiate the power stroke of the pneumatic actuator.

2. The apparatus defined in claim 1 wherein the first mechanical linkage comprises:
    a yoke member driven by the pneumatic actuator and having two spaced arms; and
    a four bar linkage having a first fixed connection, a second connection opposite the first connection and attached to the first actuator member, and third and fourth laterally spaced connections intermediate the first and second connections, each arm of the yoke member acting on the four bar linkage adjacent a respective one of the third and fourth connections to cause the third and fourth connections to move toward one another during the first part of the power stroke of the pneumatic actuator and to remain at a fixed spacing during the second part of the power stroke of the pneumatic actuator.

3. The apparatus defined in claim 2 wherein the facing inner surfaces of the arms of the yoke member operate on the four bar linkage during at least a portion of the power stroke of the pneumatic actuator and wherein the surfaces comprise cam surfaces for progressively increasing the mechanical advantage of the first mechanical linkage.

4. The apparatus defined in claim 3 wherein the yoke cam surfaces comprise first synclinal portions for operating on the four bar linkage during the first part of the power stroke of the pneumatic actuator to produce motion of the second connection of the four bar linkage away from the first connection of that linkage, and second substantially parallel portions for operating on the four bar linkage during the second part of the power stroke of the pneumatic actuator to hold the position of the second connection of the four bar linkage.

5. The apparatus defined in claim 2 wherein the second mechanical linkage comprises a surface on the yoke member for contacting the second actuator member only after completion of the first part of the power stroke of the pneumatic actuator.

6. The apparatus defined in claim 1 wherein the second actuator member is connected to the first actuator member so that the second actuator member moves with the first actuator member during the manually and pneumatically powered motion of the first actuator member and so that the second mechanical linkage can continue to move the second actuator member relative to the first actuator member after the first actuator member has stopped.

7. The apparatus defined in claim 6 wherein the means responsive to a predetermined manually produced motion of the first actuator member stops the release of pressurized gas from the gas supply and vents the pneumatic actuator after a predetermined pneumatically produced motion of the second actuator member.

8. The apparatus defined in claim 7 wherein the means responsive to a predetermined manually produced motion of the first actuator member comprises:
   a cam surface mounted on the second actuator member; and
   a cam follower operatively related to the second actuator cam surface for controlling release of pressurized gas from the gas supply and venting of the pneumatic actuator.

9. The apparatus defined in claim 8 further comprising means for returning the first and second actuator members to their initial positions when the pneumatic actuator is vented.

10. The apparatus defined in claim 9 wherein the means for returning the first and second actuator members to their initial positions comprises at least one return spring which is energized during the manually and pneumatically produced motion of the first and second actuator members.

11. The apparatus defined in claim 9 wherein the second actuator cam surface comprises substantially parallel co-terminal forward and return paths, wherein the cam follower follows the forward path during the manually and pneumatically produced motion of the first and second actuator members and follows the return path during the return motion of those members, wherein the forward path causes the cam follower to release pressurized gas from the gas supply after an initial portion associated with the manually produced motion of the first actuator member and until just before the end the forward path, and wherein the return path allows the cam follower to return to the initial portion of the forward path without causing further release of pressurized gas from the gas supply.

12. The apparatus defined in claim 1 wherein the manually produced motion of the first actuator member is reversible if stopped prior to release of pressurized gas from the gas supply.

13. The apparatus defined in claim 1 comprising means for interrupting the pneumatically produced operation of the apparatus by venting the pneumatic actuator.

14. The apparatus defined in claim 1 wherein the pressure of the gas in the gas supply is less than 200 p.s.i.g.

15. The apparatus defined in claim 14 wherein the pressure of the gas in the gas supply is in the range from 40 to 80 p.s.i.g.

16. The apparatus defined in claim 1 wherein the actuator is disposable after use in a single surgical procedure.

17. Apparatus for ligating and dividing body tissue comprising:
   an anvil assembly;
   first means for clamping the tissue to be ligated and divided against the anvil assembly and then advancing two spaced staple-like metal ligatures toward the tissue and crimping the ligatures around the tissue against the anvil assembly;
   second means for cutting the tissue between the ligatures;
   first and second movably mounted actuator members for respectively actuating the first and second means;
   a pneumatic system including a supply of pressurized gas and a pneumatic actuator pneumatically connected to the gas supply;
   a first mechanical linkage for mechanically connecting the pneumatic actuator to the first actuator member for moving the first actuator member to actuate the first means during an initial first part of the power stroke of the pneumatic actuator and for holding the first actuator member stationary during a subsequent second part of the power stroke of the pneumatic actuator;
   a second mechanical linkage for connecting the pneumatic actuator to the second actuator member for moving the second actuator member relative to the first actuator member to actuate the second means during the second part of the power stroke of the pneumatic actuator;
   third means for manually initiating motion of the first actuator member to at least initiate clamping of the tissue by the first means; and
   fourth means responsive to a predetermined manually produced motion of the first actuator member beyond the motion which at least initiates clamping of the tissue by the first means for releasing pressurized gas from the gas supply to initiate the power stroke of the pneumatic actuator.

* * * * *